United States Patent [19]
Jourdan et al.

[11] Patent Number: 5,912,729
[45] Date of Patent: Jun. 15, 1999

[54] MEASUREMENT OF PLASTIC FOAM CELL SIZE USING A VISUALIZATION TECHNIQUE

[75] Inventors: Jerome S. Jourdan, Wyandotte; Michael L. Iglehart, Trenton; Kurt A. Reimann, Grosse Ile, all of Mich.

[73] Assignee: BASF Corporation, Mt. Olive, N.J.

[21] Appl. No.: 08/664,906

[22] Filed: Jun. 17, 1996

[51] Int. Cl.⁶ .................................................. G01N 1/00
[52] U.S. Cl. .............................................................. 356/36
[58] Field of Search .................................. 356/239, 335, 356/376, 448, 446, 36

[56] References Cited

U.S. PATENT DOCUMENTS

| | | | |
|---|---|---|---|
| 3,865,488 | 2/1975 | Del Rio | 356/71 |
| 3,953,739 | 4/1976 | Colombo et al. | |
| 4,329,052 | 11/1982 | Colombo et al. | 356/335 |
| 4,412,961 | 11/1983 | Dibiasi et al. | 356/448 X |
| 5,328,935 | 7/1994 | Van Phan et al. | |
| 5,500,737 | 3/1996 | Donaldson et al. | 356/376 |

*Primary Examiner*—K Hantis
*Attorney, Agent, or Firm*—Fernando A. Borrego

[57] ABSTRACT

A method of measuring cell size of an open cell foam sample is provided including the step of providing an amount of a material suitable for obtaining foam sample impressions upon at least partial hardening in a vessel. A foam sample is placed on a surface of the material prior to hardening of the material. The foam sample is peeled away from the material after the material has begun to harden in order to provide a three-dimensional impression of at least a layer of the foam sample including a plurality of partial spherical impressions corresponding to cells of the foam sample. The cell size is measured by measuring a diameter of a plurality of the partial spherical impressions.

10 Claims, 2 Drawing Sheets

MEASUREMENT OF PLASTIC FOAM CELL SIZE USING A VISUALIZATION TECHNIQUE

BACKGROUND OF THE INVENTION

1. Field of the Invention

The present invention relates to the measurement of the size of cells or pores, such as plastic foam cell size, and more particularly, to the measurement of plastic foam cell size using a wax impression visualization technique.

2. Description of Background Art

Cells in plastic foams are typically in the form of voids or gas filled cavities formed throughout the foam. These cells are geometrically defined by the foam's composition having an overall form similar to that of a honeycomb. Cell size measurements for plastic foams such as polyurethanes, for example, are useful as a development tool to help application scientists produce foams with more desirable physical properties, in the quality control of foam manufacture and, in some cases, as an aid in setting foam specifications for sale or purchase. Cell size measurements include whole cell dimensions (maximum and minimum diameter), cell window dimensions, cell strut lengths and widths, cell size distributions, and the number count of cells falling along a straight line, e.g. cells per inch. Cell struts are the relatively thick sections of solid material that act as a foam's backbone. Cell windows are the thin, usually transparent, sections of solid material between cell struts in closed cell foams and are small openings between struts in open cell foams. There are typically 8–14 windows on the surface of a single cell. The physical properties of foams are generally believed to depend upon the structure of both the polymer network, i.e. the chemistry and morphology of the foam and the cells formed at the end of the expansion process.

One of the most common quantitative measurements of plastic foams is that of cell size. This, however, is not without some ambiguity with respect to the concept of the cell, particularly in open cell foams. Close visual inspection of a foamed polymer reinforces the difficulty inherent in defining a cell. The measurement problem is further complicated by the limited number of potentially valid linear measurements available to define a cell. These range from a direct linear measure of the maximum dimension of a cell face or edge, to a calculated size from an average of cord lengths, to a more detailed measurement of intercepts as these terms are understood by those skilled in the plastic foam art.

Some of the existing methods or techniques for the measurement of plastic foams include: (1) manual measurement of cell dimensions using optical microscopy; (2) manual counting of the number of cells along a fixed length employing optical microscopy; (3) visual comparison with an accepted standard foam utilizing optical microscopy; (4) visual comparison with an optical grid of known dimensions using microscope; (5) measurement as above after enhancing the foams surface for visualization by coloring, dying, or dusting; (6) measurement after visualization by projecting the image of a thin slice of foam on a screen; (7) indirect diameter calculations via strut length measurements by optical microscope; (8) measurement with the aid of a scanning electron microscopy (SEM) after appropriate sample preparation (gold coating); and (9) measurement with an optical microscope after enhancement by embedding the foam sample in a plastic resin, curing, cutting, and polishing the specimen.

Difficulties in the measurement of cell size in plastic foams are that the simpler or faster methods such as methods 1–6 listed above, often lead to inaccurate results and, moreover, are generally not reproducible because there is a high level of operator interpretation required. Optical microscopic analysis of foams also has the disadvantage that it is difficult to resolve cells in a three-dimensional foam lattice due to light scattering and depth of field limitations preventing a sharp focus of the cells. Furthermore, the inability to adequately measure cells with missing or distorted cell features like broken struts is also a problem. Finally, the inability to distinguish between full cells and the cell windows which make up the cells also contribute to the inaccurate results of optical microscopic analysis of cellular foams.

The method of indirect diameter calculation via strut length measurements by optical microscopy (method 7) is based on a mathematical model of the cell structure and can give a reasonable representation of cell diameters for well ordered foam samples, however, mathematical models are not well suited for foams which are not well ordered or where there is a fairly wide distribution of cell sizes.

More accurate and reproducible methods such as the use of scanning electron microscopy and enhancement by embedding the foam sample in a plastic resin, curing, cutting, and polishing the specimen (methods 8 and 9) require expensive instrumentation (SEM) or take an extended amount of time for sample analysis, typically greater than one operator hour per sample. Further, such methods, while generally more accurate than other methods, still do not necessarily provide for highly accurate measurements of foam cell components. Such methods are useful for periodic or occasional measurements for research and development purposes but are generally not suited for large numbers of samples.

Accordingly, it is desirable in the art of foam cell testing and analysis to provide a measurement technique for measuring cell size of a plastic foam which is accurate, reproducible, inexpensive, and requires a relatively small amount of time per sample.

SUMMARY OF THE INVENTION

The present invention provides a technique for measuring all cell sizes of plastic foam which is accurate, reproducible, inexpensive, and requires a relatively small amount of time per sample. These and other objects of the present invention are obtained by providing a method of measuring cell size of a plastic foam sample, comprising the steps of: providing an amount of a liquid material suitable for obtaining foam sample impressions in a vessel; placing a foam sample in contact with said material prior to hardening of said material; pealing off said foam sample from said material after said material has begun to harden or has hardened in order to provide a three-dimensional impression of at least one layer of said foam sample including a plurality of partial quasi-spherical impressions corresponding to cells of said foam sample; and measuring said cell size by measuring a diameter of a plurality of said quasi-spherical impressions.

The step of measuring the cell size may be performed by taking a micrograph of a surface of the three-dimensional wax impression of the top layers of the foam sample and measuring a diameter of the quasi-spherical impressions from the micrograph. Optionally, the wax impression can be analyzed with the aid of an image analysis software program which will perform automated cell dimension measurements. Because the wax fills the cells at their widest diameter, a highly accurate and reproducible average cell size can be determined. Also the problem of distinguishing between cells and windows is solved by the method of the present invention since only the space within a cell will be reproduced in the wax impression.

Further scope of applicability of the present invention will become apparent from the detailed description provided hereinafter. It should be understood however that the detailed description and specific examples, while indicating preferred embodiments of the invention, are intended for purposes of illustration only, since various changes and modifications within the spirit and scope of the invention will become apparent to those skilled in the art from this detailed description. For example, while the methods of the present invention are extremely useful for measuring cell size for cells typically associated with thermosetting foams, it may find utility with other types of celled materials.

BRIEF DESCRIPTION OF THE DRAWINGS

The present invention will become more fully understood from the detailed description and the accompanying drawings wherein.

DETAILED DESCRIPTION OF THE PREFERRED EMBODIMENTS

The present invention involves the use of a wax, or other hardenable fluid or flowable substance that can harden under the proper conditions, to make a three-dimensional impression of the desired section of a cellular plastic foam sample. The wax impression can then be analyzed using a simple, low power microscope, and transmitted light source with manual measurement techniques. Alternatively, the wax impression can be analyzed with the aid of image analysis software which will perform automated cell dimension measurements.

Figure 1:
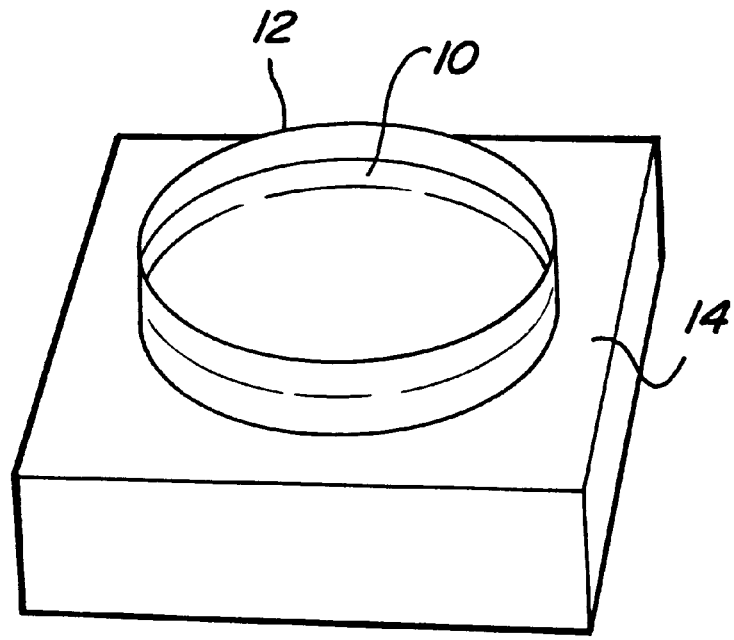
FIG. 1 is a perspective view of a vessel containing wax being heated on a hot plate.

Referring to FIG. 1, a small amount of suitable material 10, such as Luwax OA® or Luwax ES9685®, produced by BASF Corporation of Mt. Olive, N.J., is melted in a vessel such as a glass Petri dish 12 using a hot plate 14 until it becomes a clear liquid. If, after melting the material 10, any residual surface bubbles exist, a hand-held gas torch can be used to sweep the surface of the material 10 with a flame in order to remove the bubbles.

Figure 2:
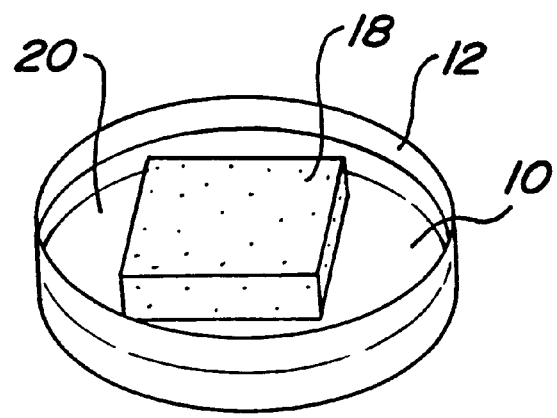
FIG. 2 illustrates a foam sample placed on a surface of the heated wax.
Figure 3:
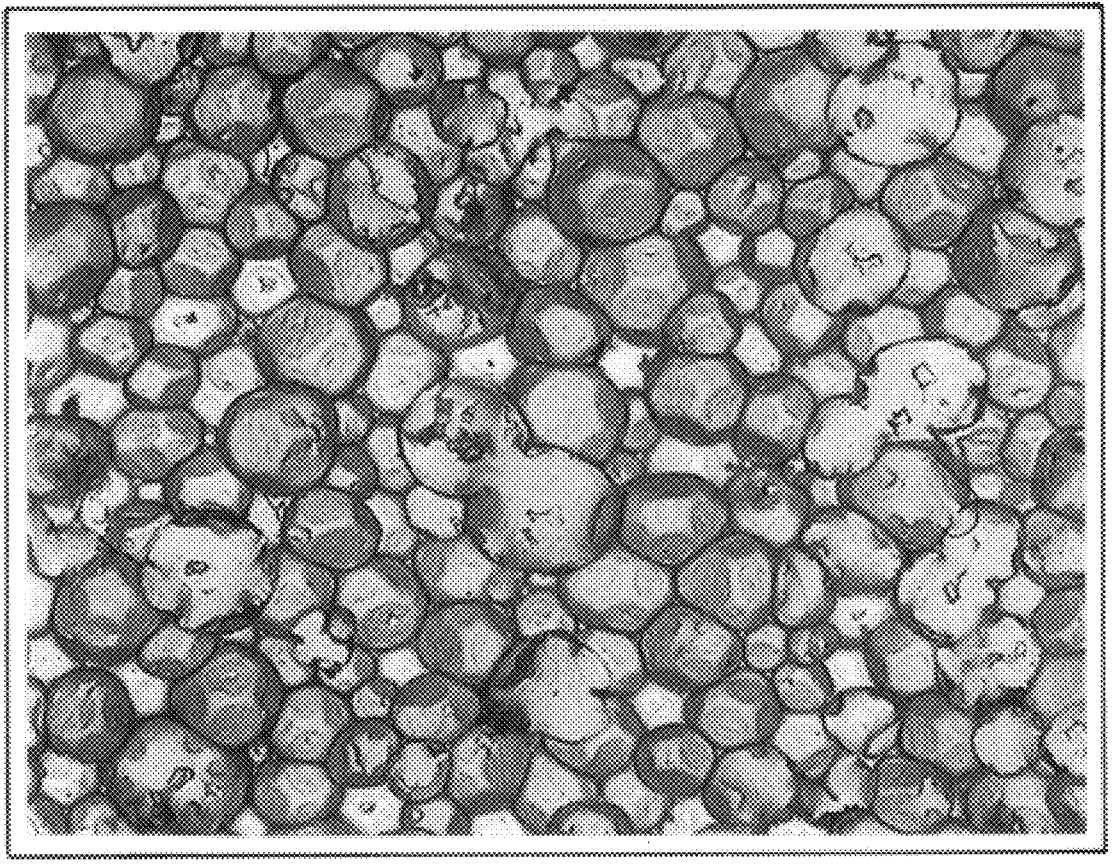
FIG. 3 is a magnified photograph of the impression formed on the surface of the wax by the foam sample.

The vessel 12 is removed from the hot plate 14 and just prior to recrystallization of the wax material 10, a section of a foam sample 18 or samples may be placed on the surface 20 of the cooling wax 10, as shown in FIG. 2. As the wax becomes absorbed by the foam sample 18, the foam typically settles into the wax to a depth of a few cell layers, i.e. for example approximately 0.1–20 mm. Typically, no additional pressure on the foam samples 18 is required. It has been found that simply and gently placing the foam samples 18 on the wax surface 20 is sufficient to produce a usable wax image. The wax 10 is allowed to cool until it begins to recrystallize (become hazy) and solidify.

The foam sample 18 is then gently peeled off of the recrystallized wax 10, leaving an impression in the wax 10. It may be necessary to pull the foam sample 18 off the cooled wax 10 at different times depending on the nature of the foam sample 18. For example, if a foam sample is particularly firm, the foam removal can be made some time after the wax has recrystallized, but with softer foams, the foam sample should be removed after the wax has recrystallized but before it has completely hardened.

When viewed under the microscope, the wax impression appears as a cluster of quasi-spherical granules which have a diameter equal to the equatorial diameter of each foam cell. This wax impression provides an image of perhaps the first one or two cell layers of the foam and produces a pseudo three-dimensional image. Photomicrographs are taken using a suitable optical microscope, e.g., a Nikon SMZ-10 stereo-zoom microscope. Optionally, a digital electronic image of the wax impressions can be made with a video microscope and stored for later analysis. Magnifications have be to adjusted to compensate for cell size, but typically, magnifications of 15x–80x are most suitable for analyzing the foam's cells.

With regard to the material used for forming the impressions(s), various considerations must be taken into account which will be clear to the skilled artisan in light of the instant teachings. If, for example, (and without limitation) a wax is employed, one should avoid using waxes which are too brittle, too soft, or too crystalline. A crystalline wax scatters more light and makes automated imaging more difficult. Waxes that produce a less transparent impression (i.e. blocks more light) are easiest to view, and potentially easier to analyze using an image analysis program. Of the many waxes tested, Luwax OA® and Luwax ES9685®, made by BASF Corporation, produced the most consistent and effective impressions. It may be necessary to use other wax types depending on the nature of the foam being tested, e.g., particularly soft foams may require a wax with a lower melting point to be effective. Luwax OA® can be characterized as an oxidized polyethylene wax having a low level of carboxyl groups along the length of the polymer chain (acid number of 20–30 and saponification number of 30–50). Its melting point is approximately 90°–100° C. with a density of about 0.96 g/cm$^3$ at 23° C. Without intending to be limited by theory, it appears that the slightly oxygenated polyethylene used in the form of Luwax OA® has the correct polarity which allows excellent capillary action into these plastic foams. Also, the melting point of the Luwax OA® family of waxes make them excellent candidates for use in the present invention.

The amount of wax used in the vessel may also be an important consideration. The thinner the wax layer, the clearer the developed image appears. However, a better image may be obtained when the solidified wax is removed from the vessel. Because there is typically a slight shrinking, (i.e. less than approximately 1.0% by volume) when the wax solidifies, there is a tendency to pull away from the vessel walls enough to facilitate simple removal. However, if the wax layer is too thin, the solidified wax may not pull away easily by itself and may tear or rip when it is manually removed. Thus, the amount of Luwax OA® employed will preferably be between 10–12 grams when the vessel utilized is a nine centimeter Petri dish. For larger and smaller foam samples, the size of the vessel may vary. Accordingly, the amount of wax necessary to facilitate easy removal is a function of the size of the vessel employed.

Although measurements of the foam itself or of the wax image can be made simply by manually measuring dimensions on photos taken through an optical microscope, this procedure is made considerably easier, faster, and more reproducible through the use of a specialized apparatus such as the RAM Optical OMIS II Video Imaging System (available from RAM Optical Instrumentation, Inc. 15192 Triton Lane, Huntington Beach, Calif. 92649). With this apparatus, a video camera is used to magnify the wax impression. The image is digitized and displayed on a video monitor. The instrumentation has built-in calibration so that at any of the magnifications available (i.e. approximately 23x to 155x) accurate measurement of the various dimensions is made easier.

After the wax impression has been prepared, it is placed on the microscope stage, brought into focus, and cell dimensions measured via a screen cross-hair tool. More particularly, the screen cross-hair tool is first placed on one edge of a foam cell, the x-axis reference obtained (i.e. zeroed), and the sample is moved so that the cross-hair is on the opposite side of the cell. Thereafter, the measurement is read from the computer screen. The measurement is recorded and the process is repeated as many times as is necessary to obtain a statistically significant sample. Typically, the wax image is marked or scored in a vertical line, then the video image is locked so that only x-axis movement is possible. Starting at the score and moving gradually to the left (or right), measurements of the maximum cell dimensions are made on all cells which fall on the single x-axis line. All the cells which happen to touch the x-axis line are counted whether or not they are equally bisected or only touch the line with the cell edge. Normally, information is collected on the first 30 cells encountered. These measurements are then averaged to obtain a value of "cells per inch".

It should also be noted that computerized image analysis can also be successfully used in analyzing the wax impressions made with the technique of the present invention. By further automating the procedure, i.e. automatically counting and measuring a large number of cells in just a few seconds, faster results can be obtained.

The wax impression visualization technique of the present invention is an inexpensive, fast, easy, and accurate way to determine the cell size and distribution of plastic foams. The cost per analysis is minimal considering the inexpensive materials used.

Sample preparation time is also minimal when compared to SEM analysis or most other methods which require sample preparation. When preparing multiple samples, the per sample preparation time can be as little as about five minutes. As stated earlier, once a wax impression has been made, measuring and recording 30 cell dimensions takes only about five minutes even if done manually. In addition, the accuracy of the technique has been illustrated and the reproducibility is approximately +/-4%, which is significantly better than other methods for examination of plastic foams.

As previously noted, the prior methods of counting the number of foam cells per linear distance suffers from the interpretation by an operator identifying "cells" and the "windows" that make up the cells. Use of a wax impression typically eliminates this problem by producing only "cells" or whole cell images for measurements.

The low thermal expansion Luwax OA® produces cells substantially equal in diameter to the "true" cell size of the foams. Problems with sectioning of foam cells is therefore eliminated, since the wax fills an entire foam cell volume. In contrast, sectioned foams generally give an artificially small average cell size because only a fraction of the total cells analyzed will have been sectioned at their widest diameter.

EXPERIMENTAL EXAMPLE

In order to demonstrate the reproducibility of the wax impression technique, an experiment is conducted using two related but different urethane foam samples which were subsequently measured by three different people. The first sample is prepared, scored once to mark a starting point along the x-axis, and the maximum diameter of the first 30 cells falling along the line are measured, and the data recorded by one person, the measurements by a second and then a third person are made over the exact same x-axis line, represented by data in Table 1 illustrated below. The starting point on the same sample is then moved and an additional triplicate series of 30 measurement points is made and recorded. A second sample is likewise analyzed. This produces a series of six averages with 30 data points for each sample. The results of the second sample are shown in Table 2 which is also reproduced below.

TABLE I

Measurements of wax impression with RAM Optical System along the x-axis line by different people.

| Technician 1 sample 1a | Technician 2 sample 1a | Technician 3 sample 1a | | Technician 1 sample 1b | Technician 2 sample 1b | Technician 3 sample 1b |
|---|---|---|---|---|---|---|
| 0.58 | 0.59 | 0.6 | | 0.3 | 0.33 | 0.68 |
| 0.26 | 0.25 | 0.26 | | 0.72 | 0.69 | 0.6 |
| 0.72 | 0.71 | 0.71 | | 0.7 | 0.7 | 0.46 |
| 0.79 | 0.78 | 0.78 | | 0.6 | 0.58 | 0.27 |
| 0.63 | 0.6 | 0.6 | | 0.6 | 0.57 | 0.55 |
| 0.59 | 0.48 | 0.5 | | 0.57 | 0.26 | 0.57 |
| 0.49 | 0.32 | 0.33 | | 0.28 | 0.56 | 0.6 |
| 0.31 | 0.56 | 0.49 | | 0.58 | 0.57 | 0.56 |
| 0.59 | 0.4 | 0.6 | | 0.39 | 0.39 | 0.45 |
| 0.5 | 0.59 | 0.37 | | 0.56 | 0.54 | 0.29 |
| 0.49 | 0.34 | 0.4 | | 0.59 | 0.57 | 0.28 |
| 0.44 | 0.38 | 0.52 | | 0.46 | 0.44 | 0.4 |
| 0.61 | 0.53 | 0.46 | | 0.48 | 0.42 | 0.41 |
| 0.59 | 0.47 | 0.6 | | 0.47 | 0.48 | 0.83 |
| 0.36 | 0.58 | 0.53 | | 0.3 | 0.42 | 0.46 |
| 0.38 | 0.52 | 0.5 | | 0.71 | 0.64 | 0.5 |
| 0.48 | 0.51 | 0.73 | | 0.46 | 0.84 | 0.49 |
| 0.4 | 0.72 | 0.21 | | 0.55 | 0.5 | 0.9 |
| 0.4 | 0.2 | 0.51 | | 0.6 | 0.9 | 0.54 |
| 0.28 | 0.53 | 0.88 | | 0.62 | 0.54 | 0.55 |
| 0.53 | 0.88 | 0.49 | | 0.82 | 0.53 | 0.65 |
| 0.5 | 0.49 | 0.49 | | 0.37 | 0.65 | 0.36 |
| 0.61 | 0.74 | 0.51 | | 0.39 | 0.4 | 0.44 |
| 0.51 | 0.5 | 0.63 | | 0.5 | 0.35 | 0.59 |
| 0.44 | 0.51 | 0.9 | | 0.87 | 0.71 | 0.49 |
| 0.49 | 0.64 | 0.6 | | 0.26 | 0.45 | 0.47 |
| 0.73 | 0.88 | 0.55 | | 0.58 | 0.65 | 0.52 |
| 0.22 | 0.6 | 0.38 | | 0.29 | 0.6 | 0.78 |
| 0.53 | 0.55 | 0.54 | | 0.56 | 0.51 | 0.34 |
| 0.84 | 0.37 | 0.6 | | 0.65 | 0.57 | 0.53 |
| 0.51 | 0.54 | 0.54 | Avgs. | 0.53 | 0.55 | 0.52 |

Overall averages for 141-1 = 0.53 mm

TABLE II

Measurements of wax impression with RAM Optical System along the same x-axis line by different people.

| Technician 1 sample 2a | Technician 2 sample 2a | Technician 3 sample 2a | Technician 1 sample 2b | Technician 2 sample 2b | Technician 3 sample 2b |
|---|---|---|---|---|---|
| 0.38 | 0.37 | 0.36 | 0.52 | 0.5 | 0.49 |
| 0.9 | 0.89 | 0.89 | 0.98 | 1 | 1 |
| 0.55 | 0.36 | 0.35 | 0.56 | 0.27 | 0.26 |
| 0.36 | 0.31 | 0.47 | 0.42 | 0.44 | 0.19 |
| 0.49 | 0.3 | 0.3 | 0.47 | 0.21 | 0.45 |
| 0.29 | 0.36 | 0.29 | 0.18 | 0.45 | 0.48 |
| 0.32 | 0.57 | 0.35 | 0.48 | 0.47 | 0.44 |
| 0.38 | 0.38 | 0.55 | 0.45 | 0.45 | 0.39 |

TABLE II-continued

Measurements of wax impression with RAM Optical System along the same x-axis line by different people.

| Technician 1 sample 2a | Technician 2 sample 2a | Technician 3 sample 2a | | Technician 1 sample 2b | Technician 2 sample 2b | Technician 3 sample 2b |
|---|---|---|---|---|---|---|
| 0.32 | 0.37 | 0.38 | | 0.4 | 0.45 | 0.43 |
| 0.57 | 0.58 | 0.31 | | 0.41 | 0.53 | 0.53 |
| 0.18 | 0.56 | 0.33 | | 0.52 | 0.47 | 0.72 |
| 0.38 | 0.53 | 0.56 | | 0.29 | 0.53 | 0.28 |
| 0.37 | 0.64 | 0.57 | | 0.41 | 0.28 | 0.51 |
| 0.74 | 0.25 | 0.41 | | 0.51 | 0.51 | 0.29 |
| 0.46 | 0.34 | 0.38 | | 0.43 | 0.39 | 0.59 |
| 0.57 | 0.56 | 0.25 | | 0.29 | 0.37 | 0.54 |
| 0.56 | 0.74 | 0.36 | | 0.56 | 0.3 | 0.4 |
| 0.42 | 0.55 | 0.53 | | 0.17 | 0.54 | 0.45 |
| 0.51 | 0.51 | 0.55 | | 0.39 | 0.51 | 0.24 |
| 0.67 | 0.53 | 0.5 | | 0.51 | 0.33 | 0.37 |
| 0.25 | 0.52 | 0.79 | | 0.38 | 0.26 | 0.28 |
| 0.35 | 0.5 | 0.54 | | 0.28 | 0.52 | 0.54 |
| 0.56 | 0.45 | 0.51 | | 0.54 | 0.54 | 0.52 |
| 0.43 | 0.53 | 0.42 | | 0.59 | 0.69 | 0.33 |
| 0.55 | 0.45 | 0.51 | | 0.52 | 0.47 | 0.57 |
| 0.5 | 0.53 | 0.52 | | 0.38 | 0.56 | 0.31 |
| 0.82 | 0.54 | 0.55 | | 0.32 | 0.58 | 0.46 |
| 0.53 | 0.54 | 0.52 | | 0.28 | 0.48 | 0.57 |
| 0.52 | 0.34 | 0.34 | | 0.5 | 0.64 | 0.57 |
| 0.53 | 0.5 | 0.5 | | 0.54 | 0.52 | 0.46 |
| 0.48 | 0.49 | 0.46 | Avgs. | 0.44 | 0.48 | 0.46 |
| | | | Overall averages for 141-2 = 0.47 mm | | | |

The reproducibility between the same individual for two data sets and for the overall sample measurement (six sets of data) is seen to be approximately +/−4.0%, e.g. 0.53 mm+/− 0.02 mm. This demonstrates excellent reproducibility for the wax impression technique of the present invention.

A series of 30 measurements are taken in approximately five minutes time once a person is familiar with the measuring technique, thereby illustrating the quickness of analysis for the technique.

A correlation study is performed using a foam sample that had been (1) photographed by an optical microscope, (2) analyzed using an SEM, and (3) imprinted using Luwax OA®. Several hundred cells from the SEM photo and the wax impression photo are hand-measured and plotted to compare cell-size distributions. The SEM photo produced a cell size distribution smaller than the wax photo, which is expected since the cells in the SEM photo had been randomly sectioned which does not generally occur at the cells' widest diameter. When a correction factor is applied by dividing the SEM diameter by 0.785 based on stereological calculations assuming a spherical cell geometry, the results from both methods correlate well.

The wax impression measurement produces a mean of 0.78 mm while the uncorrected SEM image based measurement gave 0.67 mm. After the correction factor is applied, the corrected SEM measurement gave 0.85 mm.

An experiment is conducted to show the accuracy of the wax impression against the original foam. To this end, a piece of urethane carpet underlay foam is cut with a sharp razor to produce a well defined corner. A photo is taken with an optical microscope then this specifically identified corner is gold coated and an SEM image is taken with the same magnification. A wax impression of the gold coated foam sample is prepared and a photo is taken of the wax. Enlargements are made of the three photos for comparison. For visual comparison, a transparency is placed over the wax impression photo and outlines of the wax cells are made. The transparency is then placed first over the original foam sample and then over the SEM image. The wax cell dimensions are almost exactly the same dimensions as in the other photos thus demonstrating that the wax impression is a true representation of the original foam.

The wax impression solves the time constraint of an SEM, and solves the problems associated with cut and broken cells. Because the wax fills the cells at their widest diameter, a true cell size can be determined. Also, the problem of distinguishing between "cells" and "windows" is solved. The wax impression technique according to the present invention, is a fast and inexpensive sample preparation technique which leads to accurate and reproducible measurements of cell dimensions.

The present invention thus offers development chemists an advancement in making new polymer chemical building blocks. Further, the present invention provides an analysis aid for technical service personnel trying to do problem solving with foams that may not perform as expected or that need development of new foam formulations. The present invention can also be beneficial to quality control personnel of foam producers trying to produce a consistent product, and quality control personnel of foam users who want to verify the consistency of their incoming foam raw materials.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of measuring cell size of a foam sample, comprising the steps of:
   providing in a vessel an amount of a material suitable for obtaining foam sample impressions;
   placing said foam sample in contact with said material such that said material is at least partially absorbed by said foam sample;
   peeling off said foam sample from said material after said material has begun to harden in order to provide a three-dimensional impression of at least one layer of said foam sample including a plurality of substantially spherical impressions corresponding to cells of said foam sample; and
   measuring said cell size by measuring the diameter of a plurality of said substantially spherical impressions.

2. The method according to claim 1, wherein said step of measuring said cell size includes the step of taking a photomicrograph of a surface of said three-dimensional impression and measuring a diameter of said substantially spherical impressions from said photomicrograph.

3. The method according to claim 1, wherein said material suitable for obtaining foam sample impressions is a wax.

4. The method according to claim 3, wherein said wax comprises an oxidized polyethylene wax having sufficient polarity for obtaining foam sample impressions.

5. A method of making an impression of a foam material useful for measuring cell diameter comprising the steps of:
   providing in a vessel an amount of a material suitable for obtaining foam sample impressions;
   placing a sample of said foam material in contact with said material prior to hardening of said material such that said material is at least partially absorbed by said foam sample; and
   peeling off said sample from said material after said material has begun to harden in order to provide a three-dimensional impression of at least a layer of said sample including a plurality of substantially spherical impressions corresponding to cells of said sample.

6. The method according to claim 5, wherein said material suitable for obtaining foam sample impressions is a wax.

7. The method according to claim 6, wherein said wax comprises an oxidized polyethylene wax having sufficient polarity for obtaining foam sample impressions.

8. An impression of a foam material, said impression being made by a method comprising the steps of:

providing in a vessel an amount of a material suitable for obtaining foam sample impressions;

placing a sample of said foam material in contact with said material prior to hardening of said material such that said material is at least partially absorbed by said foam sample; and peeling off said sample from said material after said material has begun to harden in order to provide a three-dimensional impression of at least a layer of said sample including a plurality of substantially spherical impressions corresponding to the cells of said sample.

9. The impression according to claim 8, wherein said material suitable for obtaining foam sample impressions is a wax.

10. The impression according to claim 9, wherein said wax comprises an oxidized polyethylene wax having sufficient polarity for obtaining sample impressions.

* * * * *